US012704491B2

(12) United States Patent
Pamulaparthy et al.

(10) Patent No.: US 12,704,491 B2
(45) Date of Patent: Aug. 11, 2026

(54) ADAPTIVE COMBINED APPROACH FOR INTELLIGENT TRANSFORMER DISSOLVED GAS ALARM DETECTION

(71) Applicant: GE Vernova Infrastructure Technology LLC, Greenville, SC (US)

(72) Inventors: Balakrishna Pamulaparthy, Hyderabad (IN); Abhishek Dey, Hyderabad (IN); Austin Byrne, Belfast (GB); Carl Wolmarans, Johannesburg (ZA)

(73) Assignee: GE VERNOVA INFRASTRUCTURE TECHNOLOGY LLC, Greenville, SC (US)

(*) Notice: Subject to any disclaimer, the term of this patent is extended or adjusted under 35 U.S.C. 154(b) by 286 days.

(21) Appl. No.: 18/654,458

(22) Filed: May 3, 2024

(65) Prior Publication Data

US 2025/0341504 A1 Nov. 6, 2025

(51) Int. Cl.
*G01N 33/00* (2006.01)
*G01N 33/28* (2006.01)
*G01R 31/62* (2020.01)

(52) U.S. Cl.
CPC ..... *G01N 33/0065* (2013.01); *G01N 33/0067* (2013.01); *G01N 33/2841* (2013.01); *G01R 31/62* (2020.01)

(58) Field of Classification Search
CPC ............... G01R 31/62; G01N 33/0065; G01N 33/0067; G01N 33/2841
See application file for complete search history.

(56) References Cited

U.S. PATENT DOCUMENTS

| | | | | |
|---|---|---|---|---|
| 10,732,164 B2 * | 8/2020 | Berler | .................. | G08B 21/182 |
| 12,100,283 B2 * | 9/2024 | Sabacinski | ............. | G08B 21/18 |
| 2017/0011612 A1 | 1/2017 | Jain | | |
| 2020/0191763 A1 | 6/2020 | Berler et al. | | |
| 2021/0102889 A1 | 4/2021 | Brauer et al. | | |

(Continued)

OTHER PUBLICATIONS

International Search Report and Written Opinion for PCT/US2025/024982, dated Jul. 16, 2025 (14 pp.).

(Continued)

*Primary Examiner* — Justin N Olamit

(74) *Attorney, Agent, or Firm* — Eversheds Sutherland (US) LLP

(57) ABSTRACT

Devices methods for triggering alarms and cautions for electrical equipment may include receiving, at edge device, data of an electrical device, including dissolved gas data or electrical data; setting, based on a comparison of a measurement value of the data to an upper rolling window-based threshold or to a lower rolling window-based threshold, a measurement flag for the electrical device; determining a rate-of-change (RoC) of the data; setting a RoC flag for the electrical device based on a comparison of the RoC to a delta RoC-based threshold; determining an acceleration of the data; setting an acceleration flag for the electrical device based on a comparison of the acceleration to a percentile log-ratio change of measurements threshold; and setting one of a no flag, a caution flag or an alarm flag for the electrical device based on the measurement flag, the RoC flag, and the acceleration flag.

18 Claims, 8 Drawing Sheets

(56) References Cited

U.S. PATENT DOCUMENTS

2023/0178270 A1* 6/2023 Dais ....................... G01R 31/62
174/139

OTHER PUBLICATIONS

Zhang, Peng, et al., "The Assess Method of Validity for DGA Sensor Based on Multiple Criterion", 2016 Electrical Insulation Conference (EIC), pp. 178-181, Jun. 19-22, 2016 (4 pp.).

Sha, Wiyan et al., "Assessment of Oil Chromatography Sensor Failure for Transformer Based on Multi-dimensional Data-driven", Journal of Physics: Conference Series, doi:10.1088/1742-6596/2560/1/012033, IPEC-1013 (10 pp.).

* cited by examiner

700

702: Raw Data
704: 75% Caution Limit
706: Standard Caution Limit
708: Standard Alarm Limit
710: 150% Alarm Limit 710
708
706
702
704

Concentration (ppm)

t1
t2
t3
t4
t6

TIME

ADAPTIVE COMBINED APPROACH FOR INTELLIGENT TRANSFORMER DISSOLVED GAS ALARM DETECTION

TECHNICAL FIELD

This disclosure generally relates to dissolved gases in power transformers, and more particularly, to alarms for dissolved gases in power transformers.

BACKGROUND

Transformer oil dissolved gas analysis is a useful, predictive, and effective way for evaluating transformer health. The breakdown of electrical insulating material and related components inside a transformer may generate gases that may be indicative of transformer faults, so detecting the gases generated may allow for transformer maintenance.

SUMMARY

A method for generating dissolved gas cautions and alarms for power transformers may include receiving, by at least one processor of an edge device, dissolved gas data of a power transformer; setting, by the at least one processor, based on a comparison of a measurement value of the dissolved gas data to an upper rolling window-based threshold or to a lower rolling window-based threshold, a gas measurement flag for the power transformer; determining, by the at least one processor, a rate-of-change (RoC) of the dissolved gas data; setting, by the at least one processor, a RoC flag for the power transformer based on a comparison of the RoC to a delta RoC-based threshold; determining, by the at least one processor, an acceleration of the dissolved gas data; setting, by the at least one processor, an acceleration flag for the power transformer based on a comparison of the acceleration to a percentile log-ratio change of measurements threshold; and setting, by the at least one processor, one of a no flag, a caution flag or an alarm flag for the power transformer based on the gas measurement flag, the RoC flag, and the acceleration flag.

An edge device for generating dissolved gas cautions and alarms for power transformers may include memory coupled to at least one processor, the at least one processor configured to: receive data of a power transformer, the data comprising dissolved gas data or electrical data; set, based on a comparison of a measurement value of the data to an upper rolling window-based threshold or to a lower rolling window-based threshold, a measurement flag for the power transformer; determine a rate-of-change (RoC) of the data; set a RoC flag for the power transformer based on a comparison of the RoC to a delta RoC-based threshold; determine an acceleration of the data; set an acceleration flag for the power transformer based on a comparison of the acceleration to a percentile log-ratio change of measurements threshold; and set one of a no flag, a caution flag or an alarm flag for the power transformer based on the measurement flag, the RoC flag, and the acceleration flag.

A method for generating dissolved gas or electrical cautions and alarms for electrical devices may include receiving, by at least one processor of an edge device, data of an electrical device, the data comprising dissolved gas data or electrical data; setting, by the at least one processor, based on a comparison of a measurement value of the data to an upper rolling window-based threshold or to a lower rolling window-based threshold, a measurement flag for the electrical device; determining, by the at least one processor, a rate-of-change (RoC) of the data; setting, by the at least one processor, a RoC flag for the electrical device based on a comparison of the RoC to a delta RoC-based threshold; determining, by the at least one processor, an acceleration of the data; setting, by the at least one processor, an acceleration flag for the electrical device based on a comparison of the acceleration to a percentile log-ratio change of measurements threshold; and setting, by the at least one processor, one of a no flag, a caution flag or an alarm flag for the electrical device based on the measurement flag, the RoC flag, and the acceleration flag.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

Figure 1:
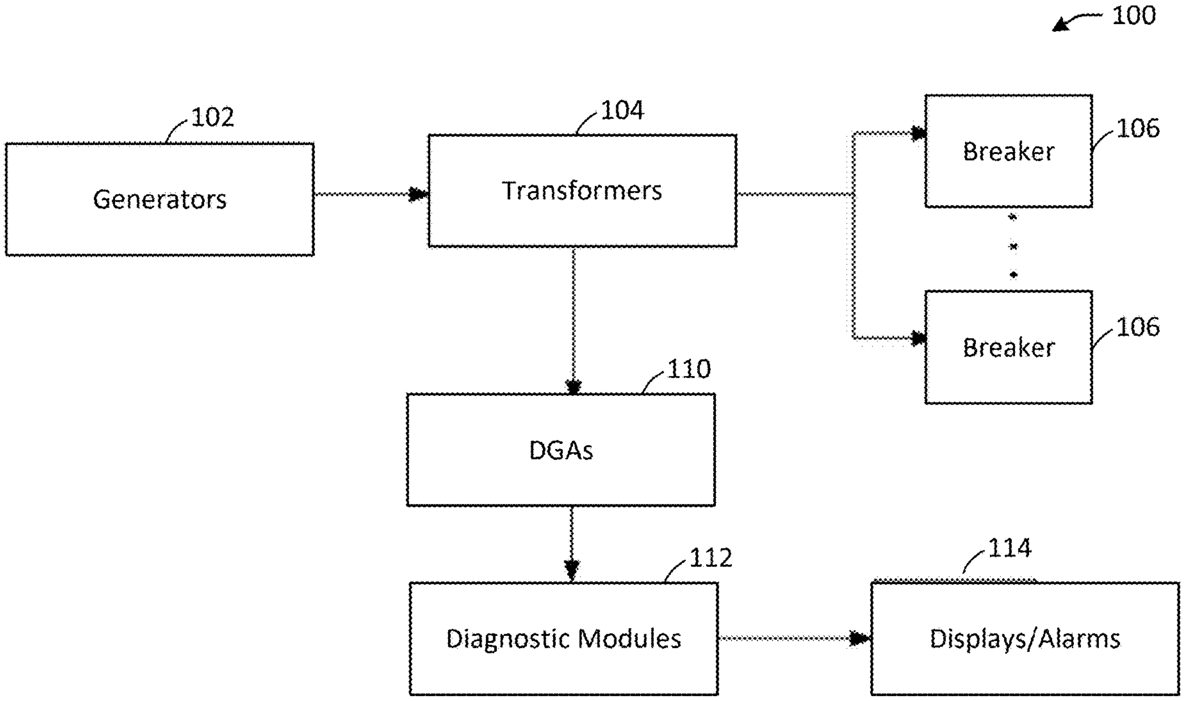
FIG. 1 illustrates an example transformer alarm system in accordance with one embodiment of the present disclosure.

Certain implementations will now be described more fully below with reference to the accompanying drawings, in which various implementations and/or aspects are shown. However, various aspects may be implemented in many different forms and should not be construed as limited to the implementations set forth herein; rather, these implementations are provided so that this disclosure will be thorough and complete, and will fully convey the scope of the disclosure to those skilled in the art. Like numbers in the figures refer to like elements throughout. Hence, if a feature is used across several drawings, the number used to identify the feature in the drawing where the feature first appeared will be used in later drawings.

DETAILED DESCRIPTION

Power transformer requires various maintenance tasks that include preventive maintenance and breakdown maintenance. Dissolved Gas Analysis (DGA) is useful in detecting and predicting transformer faults determining the maintenance on ad-hoc basis that is as required. However, DGA may generate false positive alarms that incorrectly indicate a transformer fault based on the presence of gases in transformers. Alarm thresholds used to detect transformer fault based on gas levels often are set manually based on established standards. For example, the IEEE and IEC standards organizations have set fixed alarm thresholds for gas concentration and their rate of change (ROC), such as IEEE-C57.104-2008. For example, the IEEE-C57.104-2008 standard recommends alarm thresholds that are generic based on its own transformer network or fleet historical data instead of those that are specific to a transformer. The IEC 60599-1999 standard provides alarm thresholds for transformer gas ROC.

However, the static alarm thresholds may result in false positives and may not be robust for grids with penetration of distributed energy resources, decarbonization, different types of loads being added, different loading characteristics of transformers, and different transformer manufacturing. Fixed alarm thresholds used in the standards may be transformer-agnostic and based on the 90th/95th percentile of thousands of same types of transformers connected in a network. As a transformer ages or experiences significant or frequent load changes, the generated gas concentrations tend to rise naturally. A possible result is a false fault alarm based on the fixed alarm thresholds resulting in transformer forced shutdown for maintenance and repair.

To avoid fault conditions and transformer breakdown, proactive maintenance may be performed based on forecasting the dissolve gases concentrations and their rate of change. Proactive maintenance may provide duration for which transformers may operate reliably and indicates the time for their servicing or replacement.

The adaptive DGA alarms herein for power transformers provide several technical advantages over existing static thresholds for outlier detection, using method as in Clark, James et al., "Adaptive Threshold for Outlier Detection on Data Streams," 2018 IEEE 5th International Conference on Data Science and Advanced Analytics. The enhanced alarm generation technique herein combines the log-ratio change of measurements with a percentile-based threshold, use the log-ratio change of measurements with delta RoC based thresholds and standard thresholds, estimate lookback window size instead of fixed window size for rolling window-based thresholds, and generate cautions based on variable rolling window-based thresholds and standard caution thresholds. As a result, the DGA alarms for power transformers herein are more accurate and result in fewer false and non-critical alarms than existing techniques.

In addition, previous DGA alarm solutions performed calculations and triggered alarms in a cloud environment, whereas the enhanced techniques herein facilitate DGA alarm generation at an edge device. In this manner, the alarm techniques herein are more computationally efficient than existing techniques, allowing the enhanced techniques herein to be implemented on edge devices. By maintaining the DGA data locally at an edge device, a cybersecurity enhancement is provided by the enhanced techniques herein, as the DGA data do not need to be uploaded to a cloud environment for DGA alarm analysis and triggering.

The enhanced techniques herein also are not limited to DGA data and DGA alarms. Other electrical data for power substations and other electrical devices and equipment, such as voltage, current, resistance, etc. may be analyzed to detect faults or other hazards, which may trigger alarms. The enhanced detection techniques with dynamic thresholds may apply to such data, rendering the analyses computationally efficient enough to be implemented at an edge device. By maintaining the data locally at an edge device, the cybersecurity enhancements also are provided by the techniques herein.

In one or more embodiments, the enhanced techniques herein relate to a method for intelligent data-based caution and alarm generation for dissolved gases or other electrical data in a power transformer. The present disclosure presents a method to generate cautions and alarms based on current and historical data of the transformer. The present disclosure proposes a method to generate cautions (e.g., outliers) based on rolling window-based thresholds with a variable lookback window. The present disclosure describes estimation of this lookback window based on historical data. Further, the present disclosure proposes a method to utilize the dynamic RoC thresholds calculated based on raw values and RoC values, and to capture the trend changes using statistical tools alongside the standard thresholds to trigger alarms. The methodology as described in herein supports caution and alarm generation for individual transformers. The disclosure also encloses a method to execute the algorithms on an edge device (e.g., rather than in a remote server, such as a cloud).

In one or more embodiments, the dynamic threshold approaches used herein may include a statistics-based window selection in which a Z-test may be performed between samples collected recently within a given minimum window, and an evolving varying window until the mean of the samples within these two windows are not significantly different statistically.

In one or more embodiments, the dynamic threshold approaches used herein may include a rolling variable window moving average that sets a dynamic threshold by taking the average of a set of measurements within a given window. In this approach, using a rolling window means the window of time considered in computing the average is of defined length, which moves forward with each new data point. The upper and lower thresholds may be a summation and subtraction of rolling window average and a scaled standard deviation, respectively.

In one or more embodiments, the dynamic threshold approaches used herein may include a L2-Norm (or other Norm) delta RoC. This threshold approach considers the rate at which the measurements are changing over time. RoC is the difference between the current measurement and the measurement from a certain number of samples ago normalized over the number of samples. The L2-Norm is a measure of the magnitude of a vector, and in this case, it is used to find the magnitude of the RoC values.

In one or more embodiments, the dynamic threshold approaches used herein may include a log-ratio change and a percentile flag. This approach combines the log-ratio change of measurements with a percentile-based threshold. The log-ratio change quantifies the relative change in measurements over time. The logarithm helps to normalize and reduce the effect of large changes. The calculated log-ratio change is compared with a percentile-based threshold. The threshold is dynamic and is calculated based on a certain percentile of the historical log-ratio change values. This percentile is configurable and can be set based on the user's tolerance for anomaly flags.

In one or more embodiments, the alarms may use a combined approach. A gas (or electrical) measurement flag may be set to true when a measurement value is greater than an upper rolling window-based threshold or lower than a lower rolling window-based threshold. A RoC flag may be set to true when the RoC value of a gas or electrical data type exceeds the delta ROC based (e.g., L2-norm or other Norm) threshold. An acceleration flag may be used to flag when a transformer (or other device) is experiencing anomalous trends according to historical data (e.g., a log-ratio change $n^{th}$ percentile threshold flag). When the gas measurement flag is set and the gas measurement value is above the scaled standard caution threshold, the measurement may be flagged as a caution. When the conditions for the RoC flag or the acceleration flag are satisfied, and the gas measurement value is greater than the maximum value in the current rolling window and above the standard alarm threshold, then the measurement may be flagged as an alarm. In this manner, unusual data may indicate a caution without an actual alarm.

In one or more embodiments, the thresholds used may be different for each type of transformer gas (or electrical data). In this manner, the alarm analysis may be performed for each gas (or electrical data type), and the alarm may be cumulative based on all or a subset of gas alarm states. As a result, distinguishing between different types of faults (e.g., causes of the alarms) based on which gases are in an alarm state may be improved.

The enhanced alarm techniques herein provide several distinctions with existing alarm threshold techniques, including the following: (1) dynamic threshold—employing dynamic thresholds that evolve with the data ensures the system remains sensitive to real anomalies while adapting to gradual changes in normal patterns. (2) RoC calculation—a system's ability to calculate and analyze the rate of change is pivotal. It provides immediate insights into how quickly the variables of interest (e.g., gas levels) are changing, which is crucial for early anomaly detection. (3) A "trend of trend" analysis—enhanced use of log-ratio changes to identify "trend of trend" patterns includes a double-layered trend analysis, which helps in understanding the underlying dynamics of the data over different time frames. (4) Integration of multiple metrics—distinctiveness of the enhanced techniques herein can be found in the use of both direct measurements (e.g., gas levels) and derived metrics (e.g., Delta ROC and "trend of trend") to flag anomalies. This multi-faceted approach enhances a system's reliability and accuracy. (5) Computational efficiency—despite the multi-faceted approach herein, the system is designed to be not computationally comprehensive, ensuring that it can run effectively on edge devices with limited processing capabilities, allowing for cybersecurity benefits as described above.

In one or more embodiments, after a caution or alarm flag is triggered, operator intervention may determine whether the flag is legitimate or a false flag. If a flag is false, the user may provide performance feedback that the algorithm may use to adjust/tune parameters for future analysis. For example, the algorithm may adjust/tune window size, nth percentile, any of the thresholds, and the like, automatically.

The above descriptions are for purposes of illustration and are not meant to be limiting. Numerous other examples, configurations, processes, etc., may exist, some of which are described in greater detail below. Example embodiments will now be described with reference to the accompanying figures.

FIG. 1 illustrates an example transformer alarm system 100 in accordance with one embodiment of the present disclosure.

Referring to FIG. 1, the transformer alarm system 100 may include a generators 102 for generating and providing power to a transformers 104. The current provided by the transformers 104 may be used to operate breakers (e.g., breaker 106, breaker 108). A DGAs 110 device may be coupled to the transformers 104 using an interface (e.g., one or more gas lines) to monitor and analyze any gas buildup inside of the transformers 104. When gas is present in the transformers 104, the DGAs 110 device may sample transformer oil periodically and execute one or more dissolved gases analysis procedures and provide DGA data to an intelligent electronic device that hosts the diagnostic modules 112. The diagnostic modules 112 may detect when DGA gas levels in the transformers 104 exceed one or more adaptive thresholds, which may be fixed (e.g., static alarm thresholds from IEEE or IEC standards) or variable (e.g., adaptive threshold generated from current and historical DGA data). When the DGA gas levels exceed or are forecasted to exceed an adaptive threshold, the diagnostic modules 112 may communicate the high DGA gas levels to a displays/alarms 114 to alert a user of the gas levels and/or times when to maintenance the transformers 104, and/or may control the transformers 104 and/or breakers to prevent unsuitable operation with the high gas levels in the transformers 104.

Figure 2:
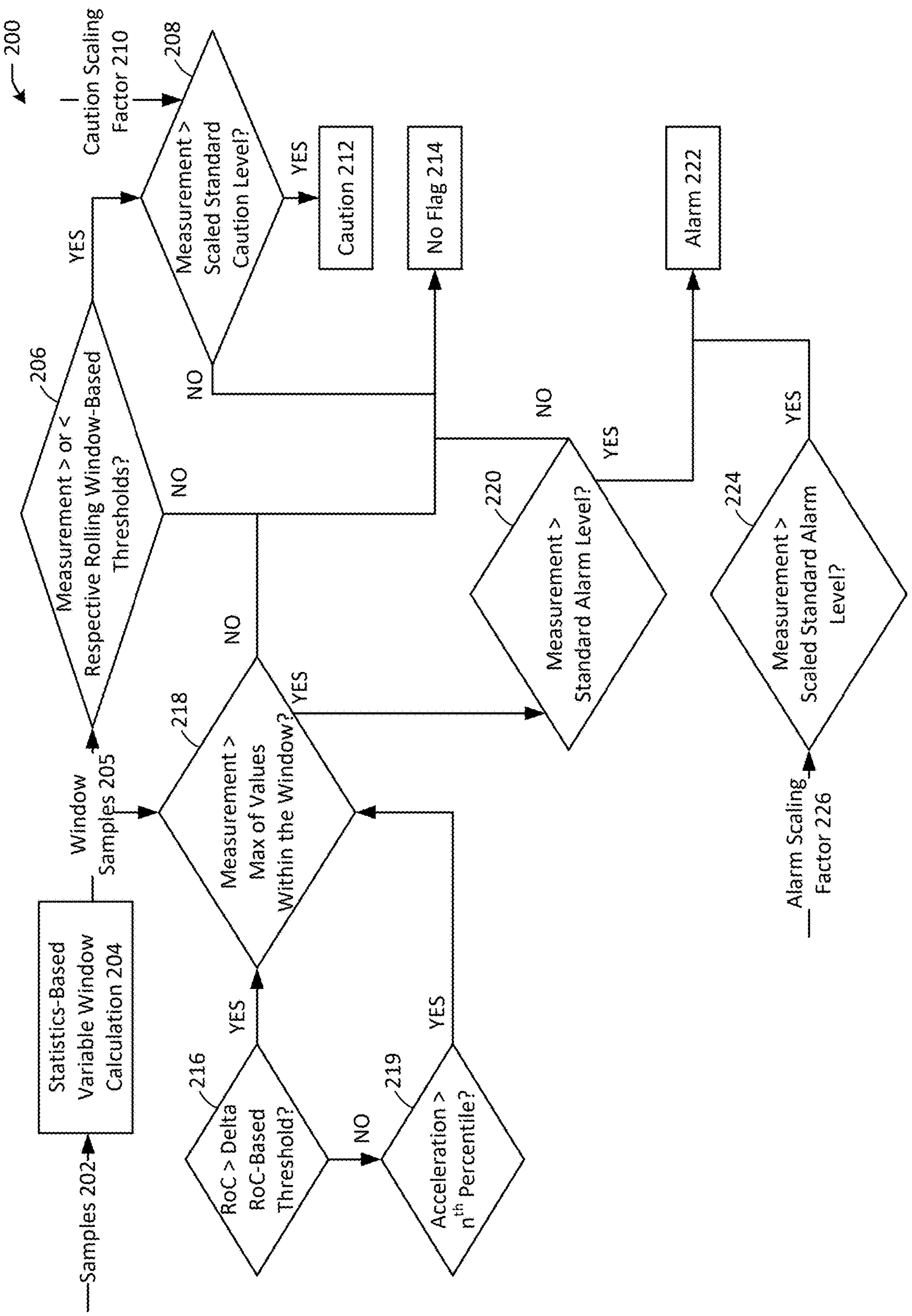
FIG. 2 illustrates an example process for triggering transformer alarms and cautions using a combined approach in accordance with one embodiment of the present disclosure.

In one or more embodiments, triggering the displays/alarms 114 may be based on the process shown in FIG. 2.

In one or more embodiments, while the example shown in FIG. 1 includes the transformers 104 and the DGAs 110, any electrical device or equipment may be monitored instead of or in addition to the transformers 104 for gases (e.g., using the DGAs 110) and/or for other electrical data (e.g., using electrical sensors and the like) according to the process in FIG. 2.

In one or more embodiments, the DGAs 110/diagnostic modules 112 or other logic used to detect alarm or caution conditions may be on edge devices rather than remote cloud devices.

FIG. 2 illustrates an example process 200 for triggering transformer alarms using a combined approach in accordance with one embodiment of the present disclosure.

Referring to FIG. 2, the process may include inputting samples 202 (e.g., gas or electrical samples from the transformers 104 or other electrical devices/equipment) to a statistics-based variable window calculation 204, which performs a statistical test (e.g., Z-test) between the samples 202 collected recently within a given minimum window and an evolving varying window until the mean of the samples 202 within these two windows (e.g., window samples 205) are not significantly different statistically. The window samples 205 may be provided to step 206 to determine whether a measurement from the samples 202 is greater than an upper rolling window-based threshold or lower than a lower rolling window-based threshold. The threshold approach at step 206 sets a dynamic threshold based on the set of measurements within a given window (e.g., of the window samples 205). In this approach, using a rolling window means the window of time considered in computing the average is of defined length which moves forward with each new data point. The upper and lower thresholds can be calculated using the statistical metrics computed based on the set of measurements within the window sample 205. When a measurement is above or below a respective rolling window-based threshold at step 206, step 208 may determine whether the measurement is greater than a scaled standard caution level (e.g., using a caution scaling factor 210, such as 75% or another number). When the measurement is above the scaled standard caution level at step 208, a caution flag 212 may be triggered. When the measurement is not above or below the respective rolling window threshold at step 206, or when the measurement is not above the scaled standard caution level at step 208, no flag 214 may be triggered (e.g., no caution or alarm flag).

Still referring to FIG. 2, at step 216, the RoC of the measurements may be determined and compared to a delta RoC based threshold (e.g., L2-norm or other norm). When the RoC is greater than the delta RoC-based threshold, step 218 may determine whether a measurement is greater than a maximum of values within the window samples 205. When the answer is no at step 218, no flag 214 may be triggered. When the RoC is not greater than the delta RoC-based threshold at step 216, step 219 may determine whether acceleration of the measurements is greater than a log-ratio based $n^{th}$ percentile threshold. When the acceleration is greater than the log-ratio based $n^{th}$ percentile threshold at step 219, the process 200 may proceed to step 218. When the measurement is greater than the maximum of values within the window samples 205 at step 218, step 220 may determine whether the measurement is greater than a standard alarm level. When the measurement is not greater than the standard alarm level at step 220, no flag 214 may be triggered. When the measurement is greater than the standard alarm level at step 220, an alarm 222 may be triggered (e.g., by the displays/alarms 114).

Still referring to FIG. 2, the process 200 may include determining, at step 224, whether a measurement is greater than a scaled standard alarm level based on an alarm scaling factor 226 (e.g., 150% or another number). When the measurement is greater than the standard alarm level based on the alarm scaling factor 226 at step 224, the alarm 22 may be triggered.

In this manner, the process 200 represents the enhanced combined approach in which when a measurement flag is set (step 206—YES) and a measurement value is above the scaled standard caution threshold at step 208, the measurement may be flagged as a caution 212. When conditions for a RoC flag is set (step 216—YES) or when the acceleration flag is set (step 219—YES), when the measurement value is greater than the maximum value in the current rolling window (step 218—YES), and when the measurement is above the standard alarm threshold (step 220 or step 224—YES), the measurement may be flagged as an alarm 222.

In one or more embodiments, the samples 202 and the measurements used in the process 200 may be gas data from the transformers 104 or other electrical equipment, or may be other electrical data from the transformers 104 or other equipment. When the data are gas data, the process 200 may be performed by the DGAs 110 and diagnostic modules 112. When the data are electrical data, the DGAs 110 and/or diagnostic modules 112 may be replaced by other computing logic capable of performing the process 200 for the electrical data instead of for gas data.

In one or more embodiments, the process 200 may be repeated for multiple gases and/or electrical data types. In this manner, the process 200 may be applied for individual gases and/or data types so that one gas and/or data type may trigger an alarm or caution, but another gas and/or other data type may not.

Figure 3:
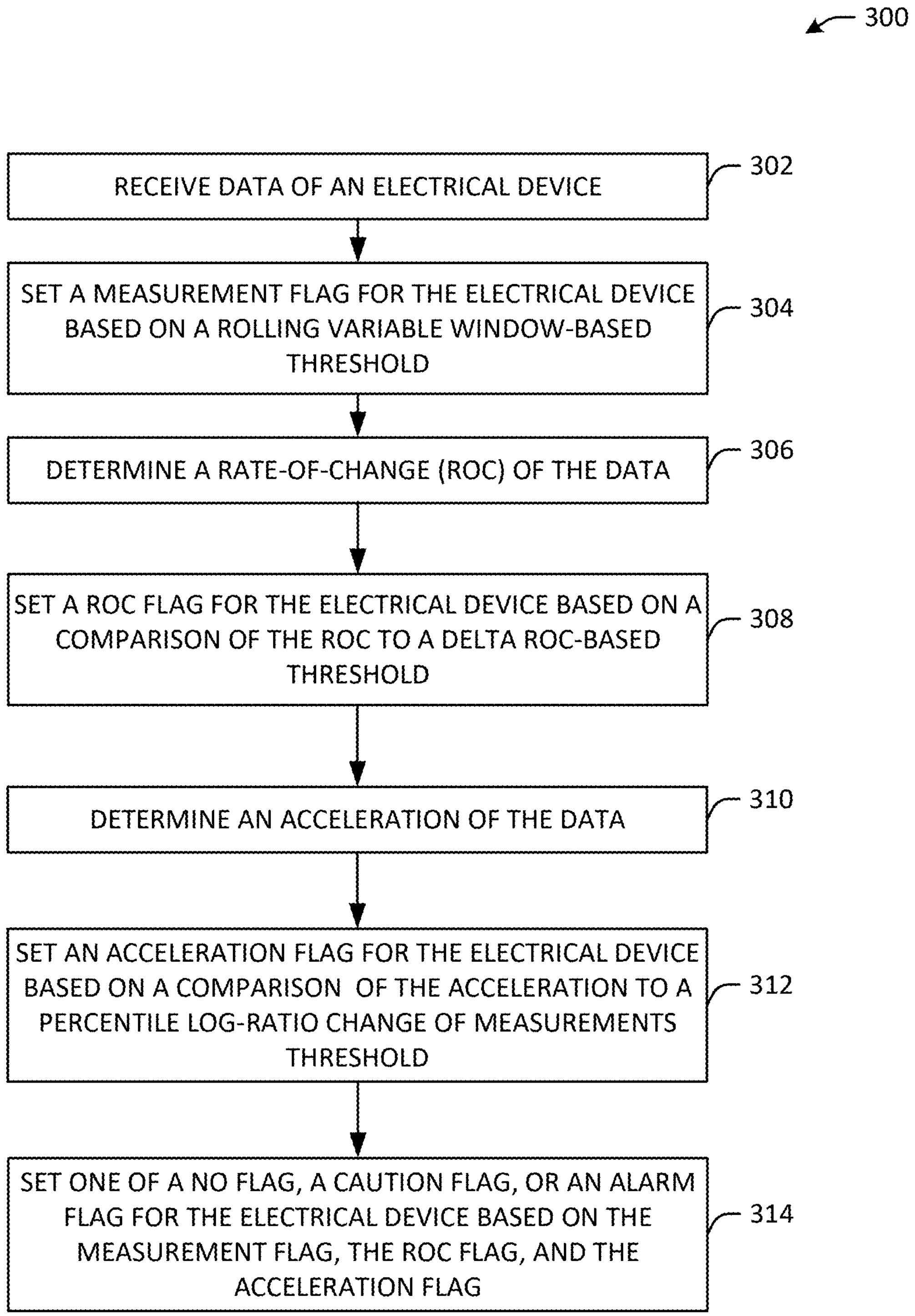
FIG. 3 illustrates an example process for triggering alarms and cautions in electrical devices using a combined approach in accordance with one embodiment of the present disclosure.

FIG. 3 illustrates an example process 300 for triggering alarms and cautions in electrical devices using a combined approach in accordance with one embodiment of the present disclosure.

At block 302, an edge device (e.g., the DGAs 110 and/or diagnostic modules 112 of FIG. 1, the alarm devices 630 of FIG. 6) may receive data of an electrical device (e.g., the transformers 104 of FIG. 1 or any type of electrical device). The data may include dissolved gas data and/or electrical data of the electrical device.

At block 304, the edge device may set a measurement flag for the electrical device. The measurement flag may be set to true is based on the measurement value being greater than the upper rolling window-based threshold or less than the lower rolling window-based threshold (e.g., step 206 of FIG. 2).

At block 306, the edge device may determine a RoC of the data. The RoC is the difference between the current measurement and the measurement from a certain number of samples ago normalized over the number of samples.

At block 308, the edge device may set a RoC flag for the electrical device based on a comparison of the RoC to a delta RoC-based threshold (e.g., step 216 of FIG. 2). For example, the threshold may be a L2-norm which is a measure of the magnitude of a vector, and it may be used to find the magnitude of the RoC values.

At block 310, the edge device may determine an acceleration of the data. The acceleration may refer to a log-ratio change of the measurements of the data over time to normalize and reduce the effect of large changes.

At block 312, the edge device may set an acceleration flag for the electrical device based on a comparison of the acceleration to a percentile log-ratio change of measurements threshold (e.g., step 219 of FIG. 2). The threshold may be dynamic and calculated based on a certain percentile of the historical log-ratio change values (e.g., $99^{th}$ percentile or another percentile). This percentile is configurable and can be set based on a user's tolerance for anomaly flags.

At block 314, the edge device may set one of a no flag, a caution flag (e.g., the caution 212 of FIG. 2) or an alarm flag (e.g., the alarm 222 of FIG. 2) based on the measurement flag, the RoC flag, and the acceleration flag. The caution flag and the alarm flag are set to false when the gas measurement flag is set to false, when (1) the gas measurement flag is set to true and the measurement value is not above a scaled standard caution threshold, (2) when the RoC flag is set to true and the measurement value is not greater than a maximum value in a current rolling time window, (3) when the RoC flag is set to true and the measurement value is greater than the maximum value in a current rolling time window and the measurement value is not greater than a standard alarm threshold, (4) when the RoC flag is false and the acceleration flag is true and the measurement value is not greater than the maximum value in a current rolling time window, and (5) when the RoC flag is false and the acceleration flag is true and the measurement value is greater than the maximum value in a current rolling time window and the measurement value is not greater than the standard alarm threshold. The caution flag is set to true when the measurement flag is set to true and when the measurement value is above a scaled standard caution threshold. The measurement flag to true is based on the measurement value being greater than the upper rolling window-based threshold or less than the lower rolling window-based threshold. The alarm flag is set to true when the RoC flag or the acceleration flag is set to true, when the measurement value is greater than a maximum value in a current rolling time window, and when the measurement value is above the standard alarm threshold. The RoC flag is set to true when the RoC is greater than the delta RoC-based threshold. The acceleration flag is set to true when the acceleration is greater than the percentile log-ratio change of measurements threshold.

Figure 4:
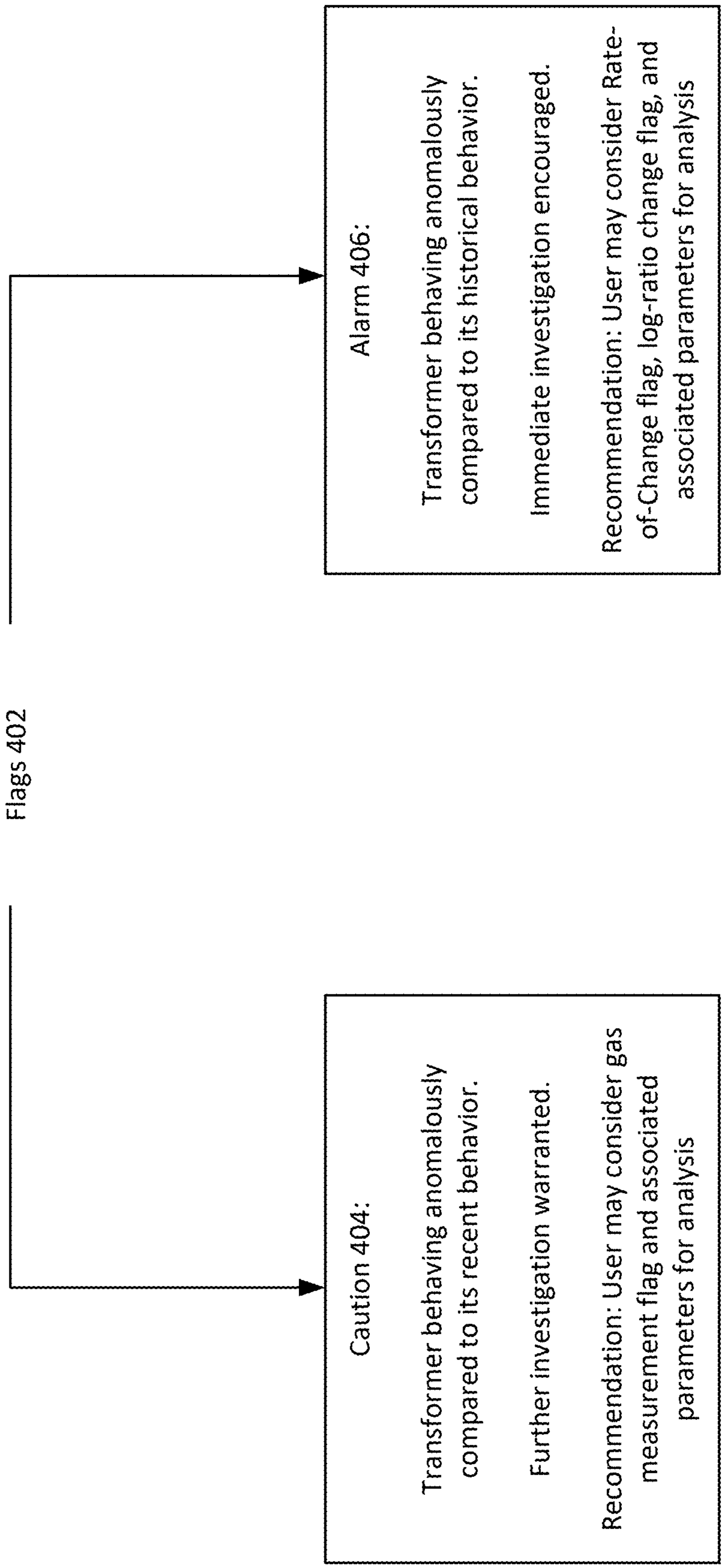
FIG. 4 shows caution flags and alarm flags in accordance with one embodiment of the present disclosure.

FIG. 4 shows caution flags and alarm flags in accordance with one embodiment of the present disclosure.

Referring to FIG. 4, flags 402 may include caution flags 404 and alarm flags 406. Caution flags 404 may indicate that a transformer (or other equipment/device) is behaving anomalously compared to its recent behavior, and that further investigation is warranted. A recommendation when a caution flag 404 is issued is for a user to consider the gas measurement flag and associated parameters for further analysis. Alarm flags 406 may indicate that a transformer (or other equipment/device) is behaving anomalously compared to its more historical behavior (e.g., a longer-term analysis than for caution flags 404), and therefore immediate investigation is encouraged. A recommendation for an alarm flag 406 is for a user to consider the RoC flag, log-ratio change flag, and other parameters for analysis.

Figure 5:
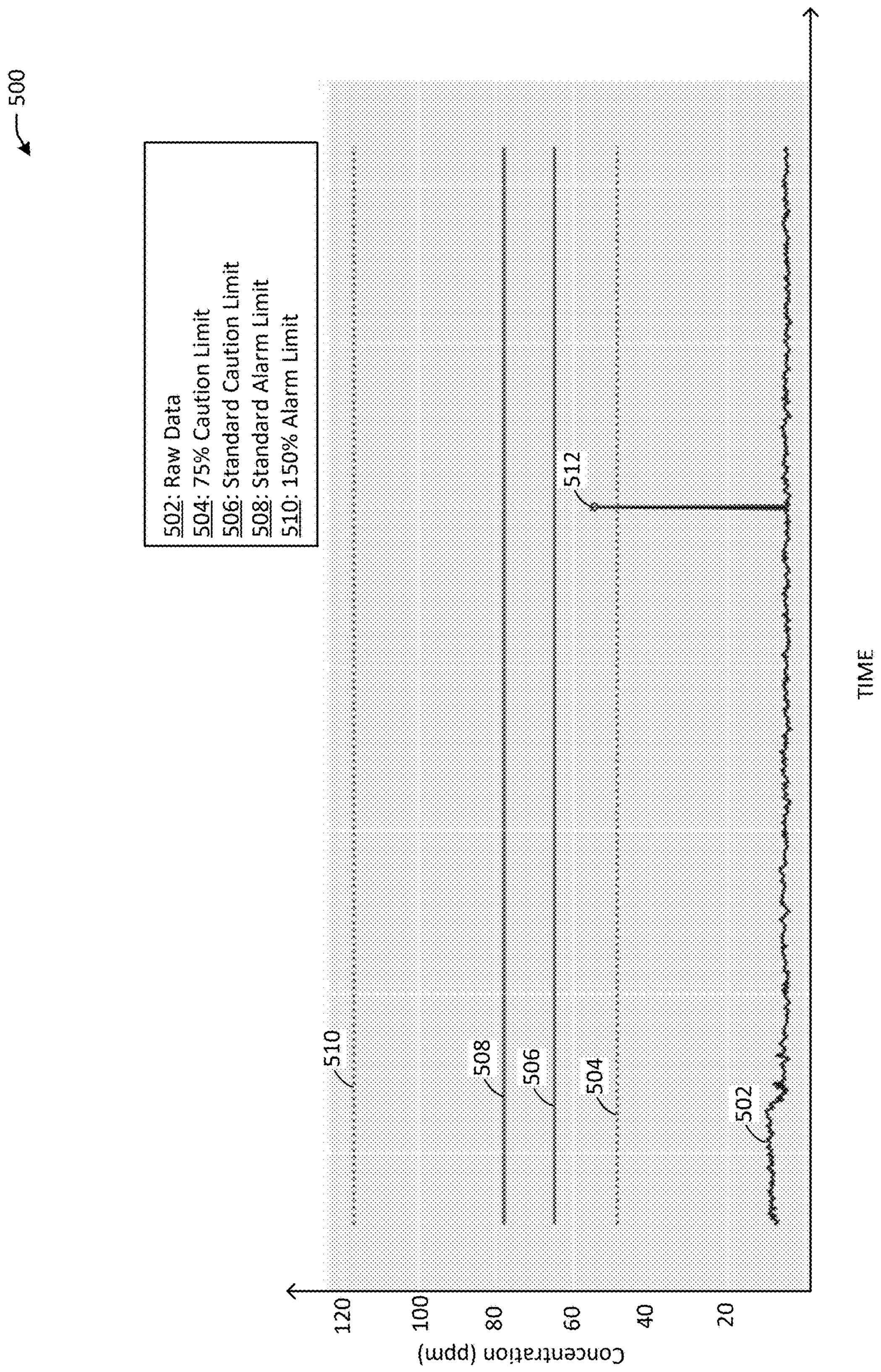
FIG. 5 is an example plot of gas concentration along with caution and alarms generated over time for a transformer using a combined approach in accordance with one embodiment of the present disclosure.

FIG. 5 is an example plot 500 of gas concentration along with caution and alarms generated over time for a transformer using a combined approach in accordance with one embodiment of the present disclosure.

Referring to FIG. 5, the plot 500 shows raw data 502 of the gas, a 75% caution limit 504, a standard caution limit 506 (e.g., greater than the 75% caution limit 504), a standard alarm limit 508, and a 150% alarm limit 510. As shown, at data point 512, the raw data 502 exceeds the 75% caution limit 504 and the gas measurement flag is set to TRUE, but not the other limits. Instead of triggering an alarm, a caution may be triggered. Even though an alarm is not triggered, the caution may indicate a need for maintenance of the transformer (e.g., of the transformers 104 of FIG. 1).

Figure 6:
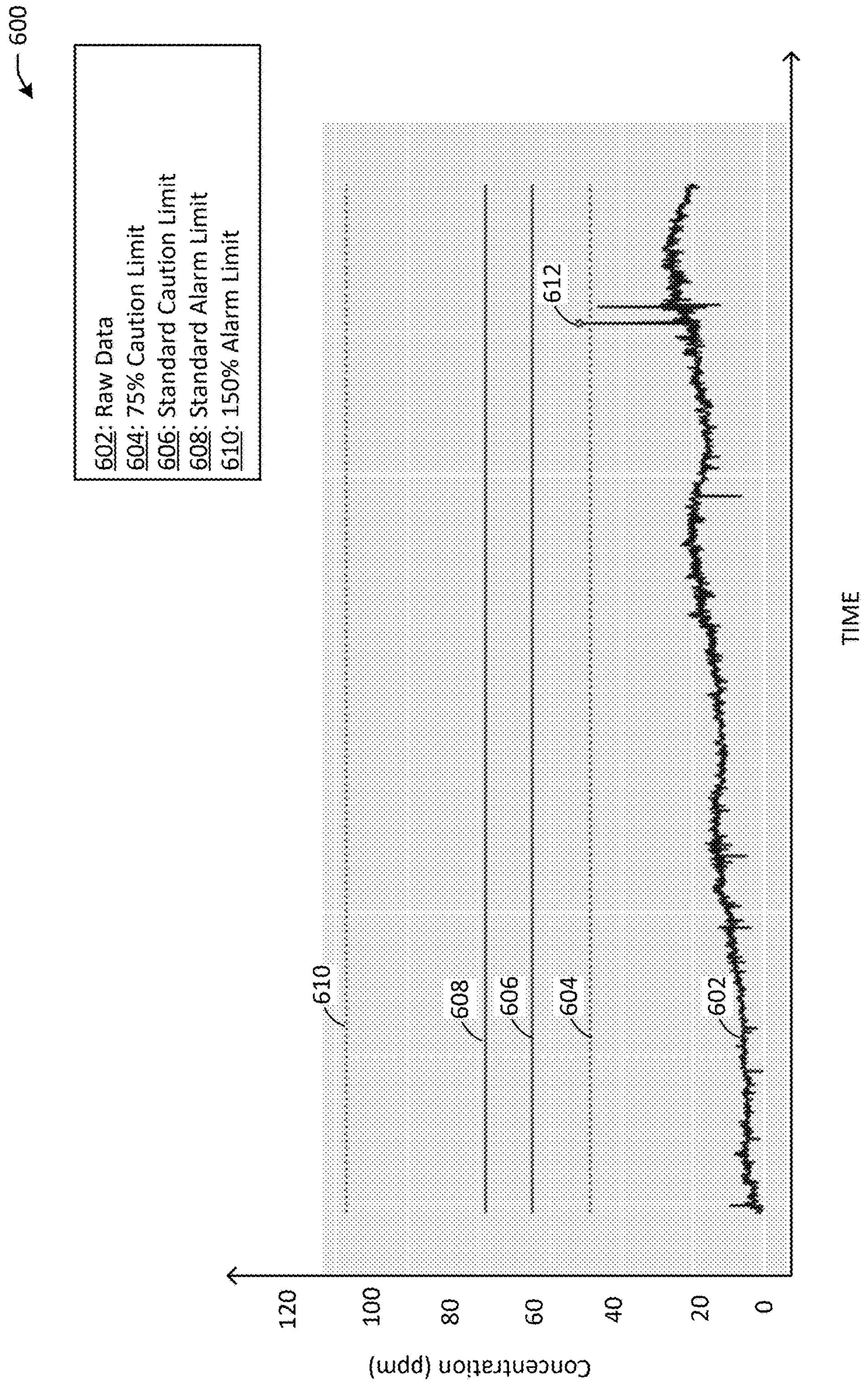
FIG. 6 is an example plot of gas concentration along with caution and alarms generated over time for a transformer using a combined approach in accordance with one embodiment of the present disclosure.

FIG. 6 is an example plot 600 of gas concentration along with caution and alarms generated over time for a transformer using a combined approach in accordance with one embodiment of the present disclosure. The transformer used in FIG. 6 may be different than the transformer in FIG. 5, which is why the plot 600 may be different than the plot 500.

Referring to FIG. 6, the plot 600 shows raw data 602 of the gas, a 75% caution limit 604, a standard caution limit 606 (e.g., greater than the 75% caution limit 604), a standard alarm limit 608, and a 150% alarm limit 610. As shown, at data point 612, the raw data 602 exceeds the 75% caution limit 604 and the gas measurement flag is set to TRUE, but not the other limits. Instead of triggering an alarm, a caution may be triggered. Even though an alarm is not triggered, the caution may indicate a need for maintenance of the transformer (e.g., of the transformers 104 of FIG. 1).

Figure 7:
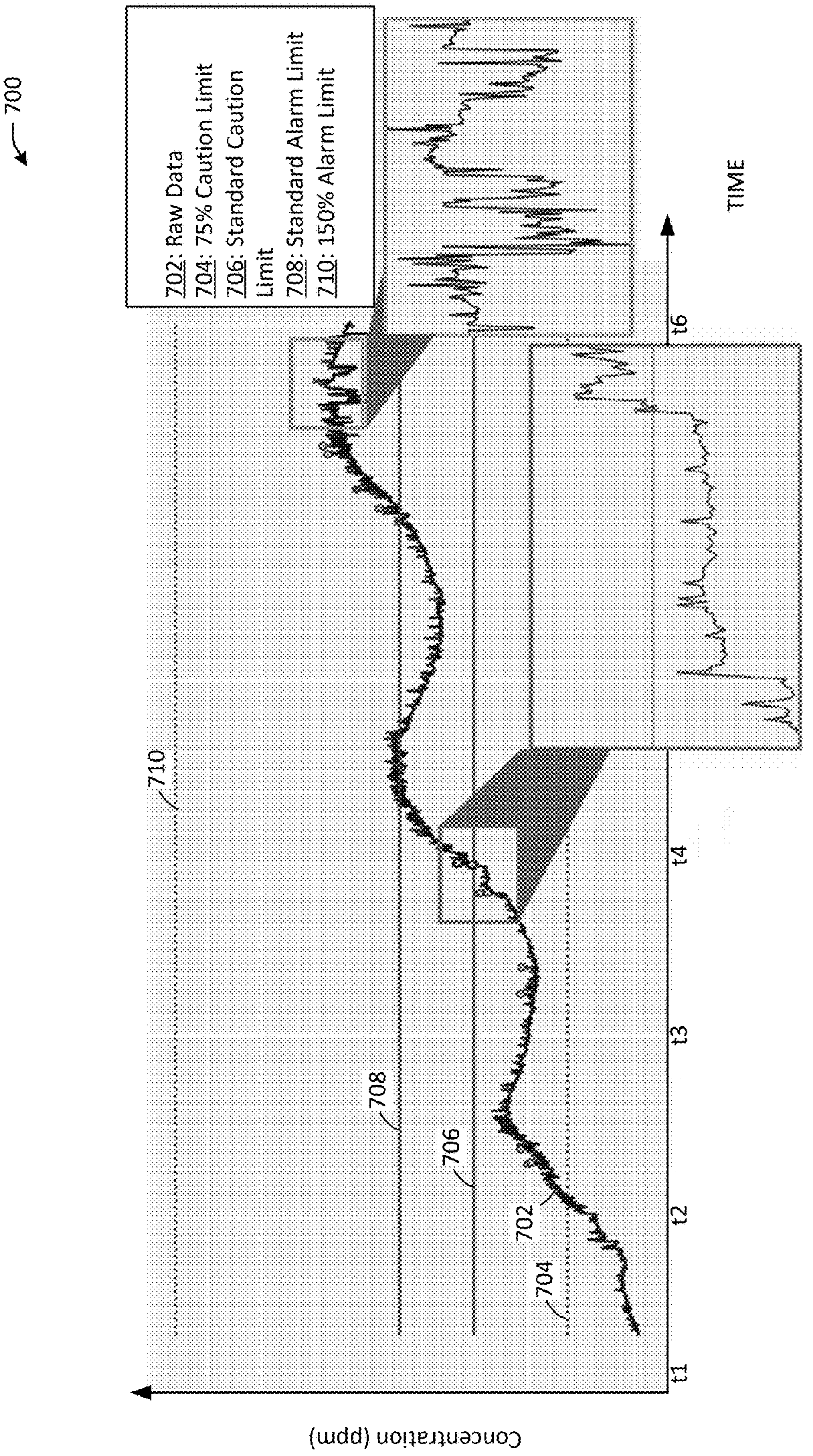
FIG. 7 is an example plot of gas concentration along with caution and alarms generated over time for a transformer using a combined approach in accordance with one embodiment of the present disclosure.

FIG. 7 is an example plot 700 of gas concentration along with caution and alarms generated over time for a transformer using a combined approach in accordance with one embodiment of the present disclosure.

Referring to FIG. 7, the plot 700 shows raw data 702 of the gas, a 75% caution limit 704, a standard caution limit 706 (e.g., greater than the 75% caution limit 704), a standard alarm limit 708, and a 150% alarm limit 710. As shown, between time t2 and time t3, between time t3 and time t4, around time t4, and around time t6, a caution flag may be triggered due to the raw data 702 exhibiting anomalies with respect to its recent behavior. When the raw data 702 exceeds the standard alarm limit 708, an alarm may be triggered when the raw data 702 exhibits behavior anomalous to its historical behavior and exceeds the standard alarm limit 708.

The examples above are not meant to be limiting.

Figure 8:
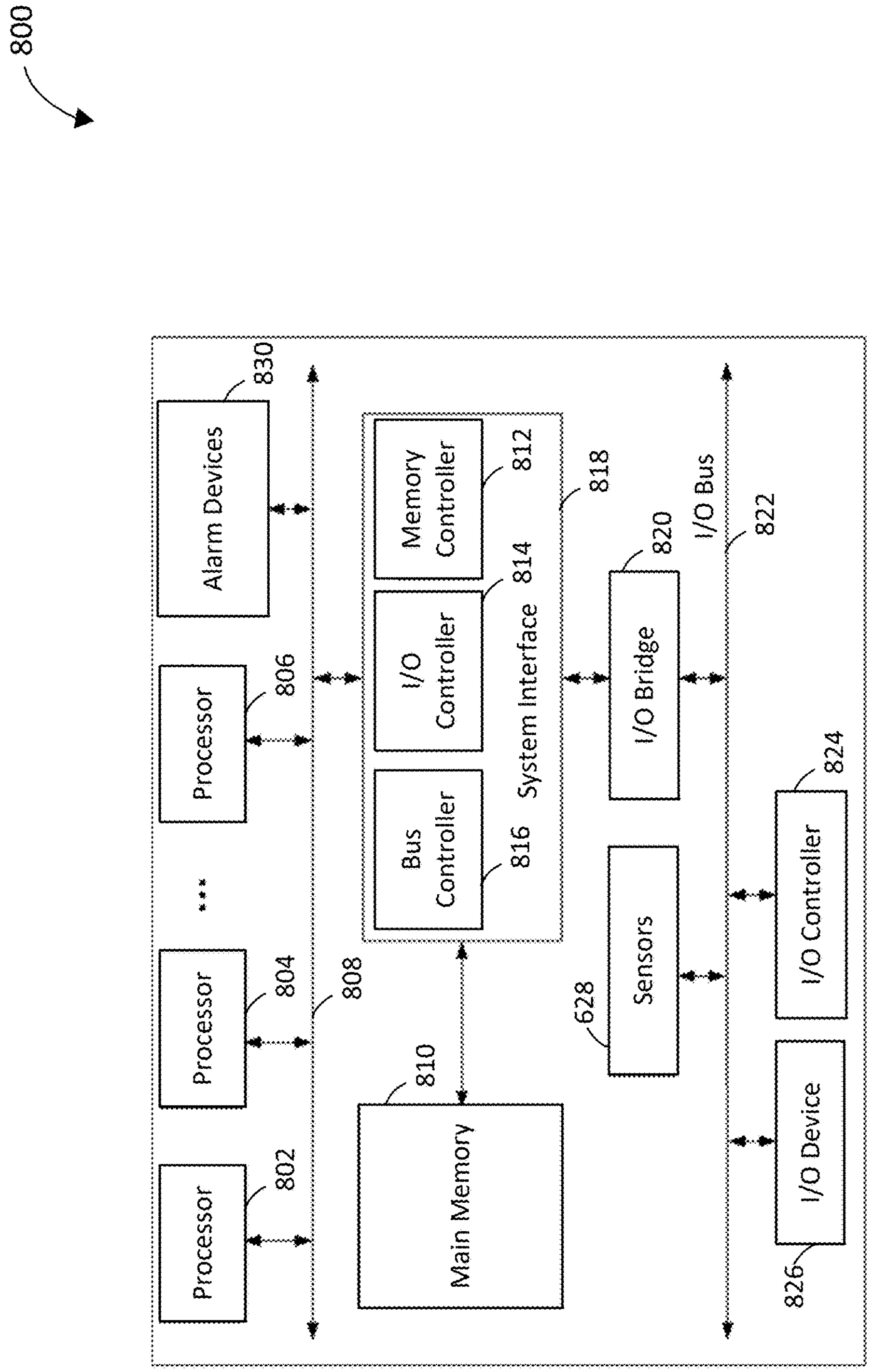
FIG. 8 is a diagram illustrating an example machine that may be used in implementing embodiments of the present disclosure.

FIG. 8 is a diagram illustrating an example machine 800 that may be used in implementing embodiments of the present disclosure. For example, the machine 800 of FIG. 8 may represent at least a portion of the transformer alarm system 100 shown in FIG. 1, as discussed above. The machine 800 includes one or more processors 802-806. Processors 802-806 may include one or more internal levels of cache (not shown) and a bus controller 816 or bus interface unit to direct interaction with the processor bus 808. Processor bus 808, also known as the host bus or the front side bus, may be used to couple the processors 802-806 with the system interface 818. System interface 818 may be connected to the processor bus 808 to interface other components of the machine 800 with the processor bus 808. For example, system interface 818 may include a memory controller 812 for interfacing a main memory 810 with the processor bus 808. The main memory 810 typically includes one or more memory cards and a control circuit (not shown). System interface 818 may also include an input/output (I/O) I/O interface 814 to interface one or more I/O bridges I/O bridge 820 or I/O devices with the processor bus 808. One or more I/O controllers and/or I/O devices may be connected with the I/O bus 822, such as I/O controller 824 and I/O device 826, as illustrated.

I/O device 826 may also include an input device (not shown), such as an alphanumeric input device, including alphanumeric and other keys for communicating information and/or command selections to the processors 802-806. Another type of user input device includes cursor control, such as a mouse, a trackball, or cursor direction keys for communicating direction information and command selections to the processors 802-806 and for controlling cursor movement on the display device.

Machine 800 may include sensors 828 for detecting dissolved gas data and/or other electrical data. For example, the sensors 828 may include total gas pressure meters, respective dissolved gas sensors for different types of dissolved gases (e.g., CO, $CO_2$, $CH_6$, $H_2$, $CH_4$, $C_2H_4$, $C_2H_6$, $C_3H_6$, $C_3H_8$, $N_2$, and others), and/or may include electrical sensors such as transducers, voltage sensors, current sensors, and the like.

Machine 800 may include alarm devices 830 capable of performing the process 200 of FIG. 2 and/or the process 300 of FIG. 3. For example, the alarm devices 830 may include modules capable of performing the functions of the DGAs 110 and/or diagnostic modules 112 of FIG. 1 and/or for measuring and setting alarm and caution flags for other electrical data of electrical equipment, power transformers or otherwise.

Machine 800 may include an adaptive storage device, referred to as main memory 810, or a random access memory (RAM) or other computer-readable devices coupled to the processor bus 808 for storing information and instructions to be executed by the processors 802-806. Main memory 810 also may be used for storing temporary variables or other intermediate information during execution of instructions by the processors 802-806. Machine 800 may include a read only memory (ROM) and/or other static storage device coupled to the processor bus 608 for storing static information and instructions for the processors 802-806. The system outlined in FIG. 8 is but one possible example of a computer system that may employ or be configured in accordance with aspects of the present disclosure.

According to one embodiment, the above techniques may be performed by machine 800 in response to processor 804 executing one or more sequences of one or more instructions contained in main memory 810. These instructions may be read into main memory 810 from another machine-readable medium, such as a storage device. Execution of the sequences of instructions contained in main memory 810 may cause processors 802-806 to perform the process steps described herein. In alternative embodiments, circuitry may be used in place of or in combination with the software instructions. Thus, embodiments of the present disclosure may include both hardware and software components.

A machine-readable medium includes any mechanism for storing or transmitting information in a form (e.g., software, processing application) readable by a machine (e.g., a computer). Such media may take the form of, but is not limited to, non-volatile media and volatile media and may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices may include volatile memory (e.g., adaptive random-access memory (DRAM), static random-access memory (SRAM), etc.) and/or non-volatile memory (e.g., read-only memory (ROM), flash memory, etc.).

Computer program products containing mechanisms to effectuate the systems and methods in accordance with the presently described technology may reside in main memory 610, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

Embodiments of the present disclosure include various steps, which are described in this specification. The steps may be performed by hardware components or may be embodied in machine-executable instructions, which may be used to cause a general-purpose or special-purpose processor programmed with the instructions to perform the steps. Alternatively, the steps may be performed by a combination of hardware, software and/or firmware.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations together with all equivalents thereof.

What is claimed is:

1. A method for generating dissolved gas cautions and alarms for power transformers, the method comprising:

receiving, by at least one processor of an edge device, dissolved gas data of a power transformer;

setting, by the at least one processor, based on a comparison of a measurement value of the dissolved gas data to an upper rolling window-based threshold or to a lower rolling window-based threshold, a gas measurement flag for the power transformer;

determining, by the at least one processor, a rate-of-change (RoC) of the dissolved gas data;

setting, by the at least one processor, a RoC flag for the power transformer based on a comparison of the RoC to a delta RoC-based threshold;

determining, by the at least one processor, an acceleration of the dissolved gas data;

setting, by the at least one processor, an acceleration flag for the power transformer based on a comparison of the acceleration to a percentile log-ratio change of measurements threshold; and setting, by the at least one processor, one of a no flag, a caution flag or an alarm flag for the power transformer based on the gas measurement flag, the RoC flag, and the acceleration flag.

2. The method of claim 1, wherein the caution flag is set to true when the gas measurement flag is set to true and when the measurement value is above a scaled standard caution threshold.

3. The method of claim 2, wherein setting the gas measurement flag to true is based on the measurement value being greater than the upper rolling window-based threshold or less than the lower rolling window-based threshold.

4. The method of claim 1, further comprising: performing, by the at least one processor, a statistical test between samples of the dissolved gas data within a minimum time window and within a varying time window until a mean of the samples within the minimum time window and the varying time window are within a statistical similarity threshold, wherein setting the gas measurement flag is based on time windows based on the mean.

5. The method of claim 1, wherein the alarm flag is set to true when the RoC flag or the acceleration flag is set to true, when the measurement value is greater than a maximum value in a current rolling time window, and when the measurement value is above a standard alarm threshold.

6. The method of claim 5, wherein the RoC flag is set to true when the RoC is greater than the delta RoC-based threshold.

7. The method of claim 5, wherein the acceleration flag is set to true when the acceleration is greater than the percentile log-ratio change of measurements threshold.

8. The method of claim 7, wherein the percentile log-ratio change of measurements threshold is dynamic, the method further comprising:

setting, by the at least one processor, the percentile log-ratio change of measurements threshold based on a percentile of log-ratio change of gas data for the power transformer.

9. The method of claim 1, wherein the measurement value is for a first type of dissolved gas, and wherein the alarm flag and the caution flag are for the first type of dissolved gas, the method further comprising:

setting, by the at least one processor, based on a comparison of a second measurement value of the dissolved gas data, for a second type of dissolved gas different than the first type of dissolved gas, to a second upper rolling window-based threshold or to a second lower rolling window-based threshold, a second gas measurement flag for the power transformer;

determining, by the at least one processor, a second RoC of the second type of dissolved gas;

setting, by the at least one processor, a second RoC flag for the power transformer based on a comparison of the second RoC to a second delta RoC-based threshold;

determining, by the at least one processor, a second acceleration of the second type of dissolved gas;

setting, by the at least one processor, a second acceleration flag for the power transformer based on a comparison of the second acceleration to a second percentile log-ratio change of measurements threshold; and setting, by the at least one processor, one of a second no flag, a second caution flag or a second alarm flag for the power transformer based on the second gas measurement flag, the second RoC flag, and the second acceleration flag.

10. The method of claim 1, wherein the caution flag or the alarm flag is set, the method further comprising:

determining that the caution flag or the alarm flag was a false flag; and adjusting, based on determining that the caution flag or the alarm flag was a false flag, at least one of the upper rolling window-based threshold, the lower rolling window-based threshold, the delta RoC-based threshold, or the percentile log-ratio change of measurements threshold.

11. An edge device for generating dissolved gas cautions and alarms for power transformers, the edge device comprising memory coupled to at least one processor, the at least one processor configured to:

receive data of a power transformer, the data comprising dissolved gas data or electrical data;

set, based on a comparison of a measurement value of the data to an upper rolling window-based threshold or to a lower rolling window-based threshold, a measurement flag for the power transformer;

determine a rate-of-change (RoC) of the data;

set a RoC flag for the power transformer based on a comparison of the RoC to a delta RoC-based threshold;

determine an acceleration of the data;

set an acceleration flag for the power transformer based on a comparison of the acceleration to a percentile log-ratio change of measurements threshold; and set one of a no flag, a caution flag or an alarm flag for the power transformer based on the measurement flag, the RoC flag, and the acceleration flag.

12. The edge device of claim 11, wherein the caution flag is set to true when the measurement flag is set to true and when the measurement value is above a scaled standard caution threshold.

13. The edge device of claim 12, wherein setting the measurement flag to true is based on the measurement value being greater than the upper rolling window-based threshold or less than the lower rolling window-based threshold.

14. The edge device of claim 11, wherein the at least one processor is configured to: perform a statistical test between samples of the dissolved gas data within a minimum time window and within a varying time window until a mean of the samples within the minimum time window and the varying time window are within a statistical similarity threshold, wherein to set the measurement flag is based on time windows based on the mean.

15. The edge device of claim 11, wherein the alarm flag is set to true when the RoC flag or the acceleration flag is set to true, when the measurement value is greater than a maximum value in a current rolling time window, and when the measurement value is above a standard alarm threshold.

16. The edge device of claim 15, wherein the RoC flag is set to true when the RoC is greater than the delta RoC-based threshold.

17. The edge device of claim 15, wherein the acceleration flag is set to true when the acceleration is greater than the percentile log-ratio change of measurements threshold.

18. A method for generating dissolved gas or electrical cautions and alarms for electrical devices, the method comprising:

receiving, by at least one processor of an edge device, data of an electrical device, the data comprising dissolved gas data or electrical data;

setting, by the at least one processor, based on a comparison of a measurement value of the data to an upper rolling window-based threshold or to a lower rolling window-based threshold, a measurement flag for the electrical device;

determining, by the at least one processor, a rate-of-change (RoC) of the data;

setting, by the at least one processor, a RoC flag for the electrical device based on a comparison of the RoC to a delta RoC-based threshold;

determining, by the at least one processor, an acceleration of the data;

setting, by the at least one processor, an acceleration flag for the electrical device based on a comparison of the acceleration to a percentile log-ratio change of measurements threshold; and setting, by the at least one processor, one of a no flag, a caution flag or an alarm flag for the electrical device based on the measurement flag, the RoC flag, and the acceleration flag.

* * * * *